US00PP20132P2

(12) United States Plant Patent
Takamura

(10) Patent No.: US PP20,132 P2
(45) Date of Patent: Jun. 30, 2009

(54) ***VIOLA* PLANT NAMED 'SUNVIOLEMO'**

(50) Latin Name: *Viola cornuta*
Varietal Denomination: Sunviolemo

(75) Inventor: Naoto Takamura, Tokyo (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/157,308

(22) Filed: Jun. 9, 2008

(51) Int. Cl.
*A01H 5/00* (2006.01)

(52) U.S. Cl. ..... Plt./323
(58) Field of Classification Search ..... Plt./323
See application file for complete search history.

*Primary Examiner*—Annette H Para
(74) *Attorney, Agent, or Firm*—C. A. Whealy

(57) ABSTRACT

A new and distinct cultivar of *Viola* plant named 'Sunviolemo', characterized by its compact, mounding and trailing plant habit; freely branching habit; freely flowering habit; and pale yellow-colored flowers.

1 Drawing Sheet

Botanical designation: *Viola cornuta.*
Cultivar denomination: 'Sunviolemo'.

BACKGROUND OF THE INVENTION

The present invention relates to a new and distinct cultivar of *Viola,* botanically known as *Viola cornuta* and hereinafter referred to by the name 'Sunviolemo'.

The new *Viola* is a product of a planned breeding program conducted by the Inventor in Higashiomi, Shiga, Japan. The objective of the breeding program was to create new compact *Viola* cultivars with attractive flower coloration.

The new *Viola* originated from a cross-pollination made by the Inventor in April, 2002, in Higashiomi, Shiga, Japan, of a proprietary selection of *Viola cornuta* identified as code number 01V-39-3, not patented, as the female, or seed, parent with a proprietary selection of *Viola cornuta* identified as code number 01 V-41-3, not patented, as the male, or pollen, parent. The new *Viola* was discovered and selected by the Inventor as a single flowering plant within the progeny of the stated cross-pollination in a controlled greenhouse environment in Higashiomi, Shiga, Japan.

Asexual reproduction of the new *Viola* by vegetative cuttings in a controlled greenhouse environment in Higashiomi, Shiga, Japan since April, 2004, has shown that the unique features of this new *Viola* are stable and reproduced true to type in successive generations.

SUMMARY OF THE INVENTION

The cultivar Sunviolemo has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunviolemo'. These characteristics in combination distinguish 'Sunviolemo' as a new and distinct cultivar of *Viola:*

1. Compact, mounding and trailing plant habit.
2. Freely branching habit.
3. Freely flowering habit.

4. Long flowering period.
5. Pale yellow-colored flowers.

Compared to plants of the female parent selection, plants of the new *Viola* differ primarily in flower color as plants of the female parent selection have darker yellow-colored flowers.

Compared to plants of the male parent selection, plants of the new *Viola* differ primarily in flower color as plants of the male parent selection have white-colored flowers.

Plants of the new *Viola* can also be compared to plants of the *Viola cornuta,* 'Sunvioki', disclosed in U.S. Plant Pat. No. 16,138. In side-by-side comparisons conducted in Higashiomi, Shiga, Japan, plants of the new *Viola* and 'Sunvioki' differed in the following characteristics:

1. Plants of the new *Viola* were narrower than plants of 'Sunvioki'.
2. Plants of the new *Viola* had shorter leaves than plants of 'Sunvioki'.
3. Plants of the new *Viola* had larger flowers than plants of 'Sunvioki'.
4. Plants of the new *Viola* and 'Sunvioki' differed in flower color.

BRIEF DESCRIPTION OF THE PHOTOGRAPHS

The accompanying colored photographs illustrate the overall appearance of the new *Viola,* showing the colors as true as it is reasonably possible to obtain in colored reproductions of this type. Colors in the photographs may differ slightly from the color values cited in the detailed botanical description which accurately describe the colors of the new *Viola.*

The photograph at the top of the sheet comprises a side perspective view of a typical flowering plant of 'Sunviolemo' grown in a container.

The photograph at the bottom of the sheet is a close-up view of typical flowers of 'Sunviolemo'.

DETAILED BOTANICAL DESCRIPTION

The aforementioned photographs and following observations, measurements and values describe plants grown in Higashiomi, Shiga, Japan, under commercial practice during the autumn in an outdoor nursery with day temperatures averaging 10° C. and night temperatures averaging 5° C. Plants had been growing for four months when the photographs and description were taken. In the following description, color references are made to The Royal Horticultural Society Colour Chart, 2001 Edition, except where general terms of ordinary dictionary significance are used.

Botanical classification: *Viola cornuta* cultivar Sunviolemo.

Parentage:

*Female, or seed, parent.*—Proprietary selection of *Viola cornuta* identified as code number 01 V-39-3, not patented.

*Male, or pollen, parent.*—Proprietary selection of *Viola cornuta* identified as code number 01 V-41-3, not patented.

Propagation:

*Type.*—By vegetative cuttings.

*Time to initiate roots.*—About two weeks at 20° C. to 25° C.

*Time to produce a rooted young plant roots.*—About four weeks at 20° C. to 25° C.

*Root description.*—Fine, fibrous and fleshy; light brown in color.

*Rooting habit.*—Freely branching.

Plant description:

*Plant form/habit.*—Compact, mounding and trailing plant habit; vigorous growth habit. Freely branching habit; about 25 lateral branches developing per plant; pinching enhances branching.

*Plant height.*—About 9.4 cm.

*Plant width (spread).*—About 29.5 cm.

*Lateral branches.*—Length: About 16.1 cm. Diameter: About 2.2 mm. Internode length: About 1.3 cm. Strength: Strong. Texture: Smooth, glabrous. Color: Close to 145A.

Foliage description:

*Arrangement.*—Alternate, simple.

*Length.*—About 2 cm.

*Width.*—About 1.4 cm.

*Shape.*—Ovate.

*Apex.*—Obtuse.

*Base.*—Obtuse.

*Margin.*—Crenate.

*Texture, upper surface.*—Pubescent.

*Texture, lower surface.*—Smooth, glabrous.

*Venation pattern.*—Pinnate; reticulate.

*Color.*—Developing and fully expanded leaves, upper surface: Close to 137C; venation, close to 145A. Developing and fully expanded leaves, lower surface: Close to 146B; venation, close to 145A.

*Petiole.*—Length: About 1.6 cm. Diameter: About 0.8 mm. Texture, upper and lower surfaces: Pubescent. Color, upper and lower surfaces: Close to 145A.

*Stipule.*—Length: About 2 cm. Diameter: About 1 cm. Shape: Pinnately-parted. Apex: Obtuse. Base: Cuneate. Texture, upper and lower surfaces: Smooth, glabrous. Color, upper and lower surfaces: Close to 137C.

Flower description:

*Flower type/habit.*—Single flowers borne in upper leaf axils; flowers face obliquely upright. Freely flowering habit with about 24 flowers per plant.

*Fragrance.*—Slightly scented; pleasant.

*Natural flowering season.*—Continuously flowering from early November to June in Japan. Flowers not persistent.

*Postproduction longevity.*—Flowers last about five to seven days on the plant.

*Flower buds.*—Height: About 1.9 cm. Diameter: About 9 mm. Shape: Lenticular. Color: Close to 154B.

*Flower diameter.*—About 4 cm by 3.4 cm.

*Flower depth.*—About 2 cm.

*Eye diameter.*—About 3.9 mm.

*Petals.*—Quantity per flower: Five in a single whorl; two upper petals, two lateral petals and one lower petal, spurred. Upper petals: Length: About 2.2 cm. Diameter: About 2.2 cm. Shape: Spatulate with rounded apex and attenuate base; margin, entire and slightly undulate. Texture, upper and lower surfaces: Smooth, glabrous; velvety. Color: Developing and fully expanded petals, upper surface: Close to 3C. Developing and fully expanded petals, lower surface: Close to 3C. Lateral petals: Length: About 1.7 cm. Diameter: About 1.6 cm. Shape: Spatulate with rounded apex and attenuate base; margin, entire and slightly undulate. Texture, upper and lower surfaces: Smooth, glabrous; velvety. Color: Developing and fully expanded petals, upper surface: Close to 3C. Developing and fully expanded petals, lower surface: Close to 3C. Lower petal: Length: About 1.6 cm. Diameter: About 2.5 cm. Shape: Reniform with cordate apex and attenuate base; margin, entire and slightly undulate. Texture, upper and lower surfaces: Smooth, glabrous; velvety. Color: Developing and fully expanded petals, upper surface: Close to 3C; stripes at base, close to N186B; towards the eye, close to 3A; eye, close to 17B. Developing and fully expanded petals, lower surface: Close to 3C. Spur length: About 5.6 mm. Spur diameter: About 2.1 mm. Spur color: Close to 90A.

*Sepals.*—Quantity per flower: Typically five in a single whorl. Length: About 1.7 cm. Width: About 4.3 mm. Shape: Lanceolate. Apex: Acute. Base: Truncate. Margin: Entire. Texture, upper and lower surfaces: Smooth, glabrous. Color, upper surface: Close to 147B. Color, lower surface: Close to 137C.

*Peduncles.*—Length: About 5.3 cm. Diameter: About 1.2 mm. Texture: Smooth, glabrous. Color: Close to 137C.

*Reproductive organs.*—Stamens: Quantity per flower: Typically five. Anther shape: Ellipsoidal. Anther size: About 1.2 mm by 0.8 mm. Anther color: Close to 1D; towards the apex, close to 175C. Pollen amount: Scarce. Pollen color: Close to 10D. Pistils: Quantity per flower: One. Pistil length: About 5 mm. Stigma shape: Ellipsoidal. Stigma color: Close to 151B. Style color: Close to 145C. Ovary color: Close to 147B.

*Seed/fruit.*—Seed and fruit development have not been observed.

Disease/pest resistance: Plants of the new *Viola* have not been noted to be resistant to pathogens and pests common to *Viola*.

Garden performance: Plants of the new *Viola* have been observed to have good garden performance and to tolerate rain, wind and temperatures from about −7° C. to about 25° C.

It is claimed:

1. A new and distinct *Viola* plant named 'Sunviolemo' as illustrated and described.

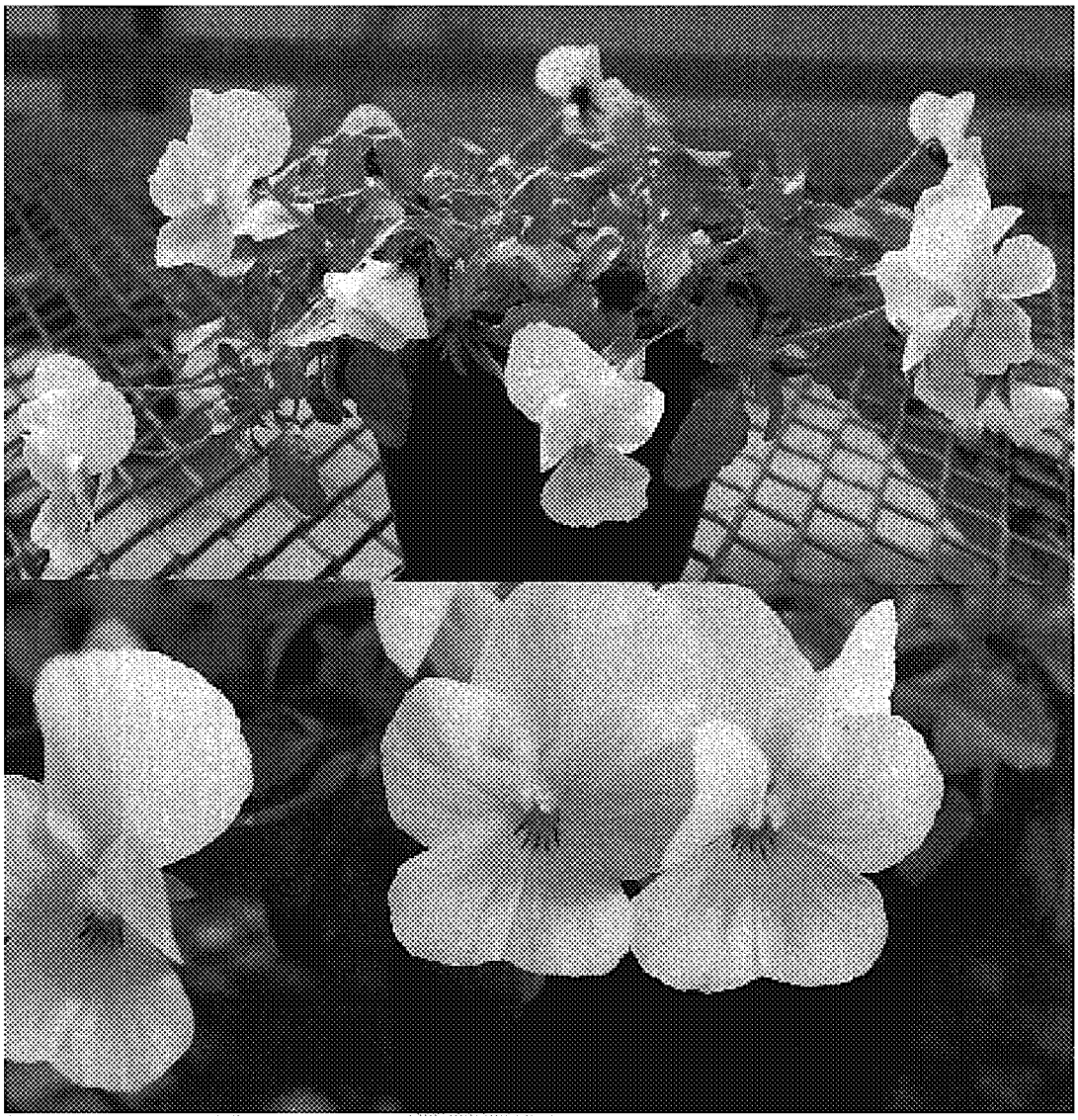

* * * * *